US00PP19015P2

(12) United States Plant Patent
Troelstra

(10) Patent No.: US PP19,015 P2
(45) Date of Patent: Jul. 15, 2008

(54) ***CORTADERIA* PLANT NAMED 'SCARLET WONDER'**

(50) Latin Name: *Cortaderia selloana*
Varietal Denomination: Scarlet Wonder

(75) Inventor: Johan Troelstra, Appelscha (NL)

(73) Assignee: Compass Plants B.V., Hillegom (NL)

( * ) Notice: Subject to any disclaimer, the term of this patent is extended or adjusted under 35 U.S.C. 154(b) by 0 days.

(21) Appl. No.: 11/705,867

(22) Filed: Feb. 14, 2007

(51) Int. Cl.
*A01H 5/00* (2006.01)

(52) U.S. Cl. ..... Plt./384
(58) Field of Classification Search ..... Plt./384
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Cortaderia* plant named 'Scarlet Wonder', characterized by its upright and somewhat outwardly spreading plant habit; vigorous growth habit; green-colored leaves; purple-colored pendulous flower panicles; and good garden performance.

1 Drawing Sheet

Botanical description: *Cortaderia selloana.*
Cultivar denomination: 'Scarlet Wonder'.

BACKGROUND OF THE INVENTION

The present invention relates to a new and distinct cultivar of *Cortaderia* plant, botanically known as *Cortaderia selloana,* and hereinafter referred to by the name 'Scarlet Wonder'.

The new *Cortaderia* is a naturally-occurring branch mutation of an unnamed selection of *Cortaderia selloana,* not patented. The new *Cortaderia* was discovered and selected by the Inventor within a population of plants of the parent selection in a controlled environment in Appelscha, The Netherlands in July, 2002.

Asexual reproduction of the new *Cortaderia* by micropropagation in Zandvoort, The Netherlands since July, 2005, has shown that the unique features of this new *Cortaderia* are stable and reproduced true to type in successive generations.

SUMMARY OF THE INVENTION

The cultivar Scarlet Wonder has not been observed under all possible environmental conditions. The phenotype may vary somewhat with variations in environment such as temperature and light intensity, without, however, any variance in genotype.

The following traits have been repeatedly observed and are determined to be the unique characteristics of 'Scarlet Wonder'. These characteristics in combination distinguish 'Scarlet Wonder' as a new and distinct cultivar of *Cortaderia:*

1. Upright and somewhat outwardly spreading plant habit.
2. Vigorous growth habit.
3. Green-colored leaves.
4. Purple-colored pendulous flower panicles.
5. Good garden performance.

Plants of the new *Cortaderia* differ from plants of the parent selection in the following characteristics:

1. Plants of the new *Cortaderia* are taller than plants of the parent selection.
2. Flower panicles of plants of the new *Cortaderia* are more pendulous than flower panicles of plants of the parent selection.
3. Flower panicles of plants of the new *Cortaderia* are red purple in color whereas flower panicles of plants of the parent selection are white in color.

Plants of the new *Cortaderia* can be compared to plants of the *Cortaderia selloana* cultivar Pumila, not patented. Plants of the new *Cortaderia* differ primarily from plants of the cultivar Pumila in flower panicle coloration as plants of the cultivar Pumila have white-colored flower panicles.

BRIEF DESCRIPTION OF THE PHOTOGRAPH

The accompanying photograph illustrates the overall appearance of the new *Cortaderia.* This photograph shows the colors as true as it is reasonably possible to obtain in colored reproductions of this type. Colors in the photograph may differ slightly from the color values cited in the detailed botanical description which accurately describe the colors of the new *Cortaderia.* The photograph comprises a side perspective view of a typical three-year old plant of 'Scarlet Wonder' grown in an outdoor nursery in Appelscha, The Netherlands.

DETAILED BOTANICAL DESCRIPTION

In the following description, color references are made to The Royal Horticultural Society Colour Chart, 2001 Edition, except where general terms of ordinary dictionary significance are used. The aforementioned photograph and following observations and measurements describe plants grown in Appelscha, The Netherlands during the autumn in an outdoor nursery and under conditions and practices which approximate those generally used in commercial *Cortaderia* production. During the production of the plants, day temperatures ranged from 12° C. to 25° C. and night temperatures ranged from 4° C. to 14° C. Measurements and numerical values for represent averages for typical three-year old plants.

Botanical classification: *Cortaderia selloana* cultivar Scarlet Wonder.

Parentage: Naturally-occurring branch mutation of an unnamed selection of *Cortaderia selloana,* not patented.

Propagation:

*Type.*—By micropropagation.

*Time to initiate roots.*—About two months at 20° C.

*Time to produce a rooted young plant.*—About six months at 20° C.

*Root description.*—Thick, fleshy; white in color.

Plant description:

*Plant form/growth habit.*—Perennial; upright and outwardly spreading plant habit; broadly inverted triangle with arching leaves and pendulous flower panicles. Vigorous growth habit.

*Plant height, including flower panicles.*—About 232 cm.

*Plant height, excluding flower panicles.*—About 164 cm.

*Plant diameter or spread.*—About 237 cm.

*Culm (stem) description.*—Quantity per plant: About 24. Shape: Cylindrical; enclosed by leaf sheaths. Length: About 59 cm. Diameter: About 1.1 cm. Internode length: About 3.9 cm. Aspect: Mostly upright. Strength: Strong. Texture: Smooth, glabrous. Color: Between 146C and 147C.

*Ligule.*—Length: About 4 mm. Color: Close to N155A.

Foliage description:

*Arrangement.*—Alternate, two-ranked, simple; leaf base sheathing the culm.

*Length (including sheath).*—About 172 cm.

*Width.*—About 1.3 cm.

*Shape.*—Linear; narrow.

*Apex.*—Long acuminate.

*Margin.*—Entire with short bristles; bristles inconspicuous.

*Aspect.*—Initially upright then outwardly arching with development.

*Texture, upper and lower surfaces.*—Mostly smooth; margins, sparsely pubsecent.

*Venation pattern.*—Parallel.

*Color.*—Developing foliage, upper surface: 138B; towards the apex, 138A; towards the base, 144B to 144C. Developing foliage, lower surface: 138A; towards the base, 144B. Fully expanded foliage, upper surface: 137B; venation, 137B. Fully expanded foliage, lower surface: 137A; towards the base, 145A; venation, 137B.

Inflorescence description:

*Arrangement.*—Numerous single flowers arranged in terminal pendulous panicles; flowers sessile.

*Fragrance.*—None detected.

*Inflorescence length.*—About 68 cm.

*Inflorescence diameter.*—About 35 cm.

*Quantity of flowers per inflorescence.*—About 20,000.

*Time to flower.*—From September into early November in The Netherlands. Individual flowers last about ten days on the plant; flowers persistent.

*Flower buds.*—Length: About 4 mm. Diameter: About 1 mm. Shape: Narrow lanceolate. Color: 183A.

*Flower diameter.*—About 4 mm.

*Flower height.*—About 5 mm.

*Glume/lemma.*—Quantity/arrangement: One glume per flower positioned at posterior of flower; two lemma positioned on either side of flower. Glume and lemma enclose immature anthers. Glume length: About 1.3 cm. Glume width: About 1 mm. Lemma length: About 5 mm. Lemma width: Less than 1 mm. Shape: Glume, linear: Lemma, fibril-shaped. Apex, glume and lemma: Narrowly acute. Margin, glume and lemma: Entire. Texture, glume and lemma: Smooth, glabrous. Color, glume and lemma, inner and outer surfaces: 156D.

*Peduncles.*—Length: About 164 cm. Diameter: About 1.7 cm. Strength: Strong. Angle: About 5° from vertical. Texture: Pubescent. Color: 146C to 146D.

*Reproductive organs.*—Androecium: Stamen quantity per flower: About two. Anther length: About 3 mm. Anther shape: Oblong; narrow. Anther color, immature: 183A. Anther color, mature: 200A to 200B. Pollen amount: Scarce. Pollen color: N167A to N167B. Gynoecium: Not observed.

*Seed/fruit.*—Seed and fruit development have not been observed.

Disease/pest resistance: Plants of the new *Cortaderia* have not between shown to be resistant to pathogens and pests common to *Cortaderia.*

Garden performance: Plants of the new *Cortaderia* have been observed to have good garden performance and tolerate wind, rain and temperatures ranging from about −10° C. to about 40° C.

It is claimed:

1. A new and distinct *Cortaderia* plant named 'Scarlet Wonder' as illustrated and described.

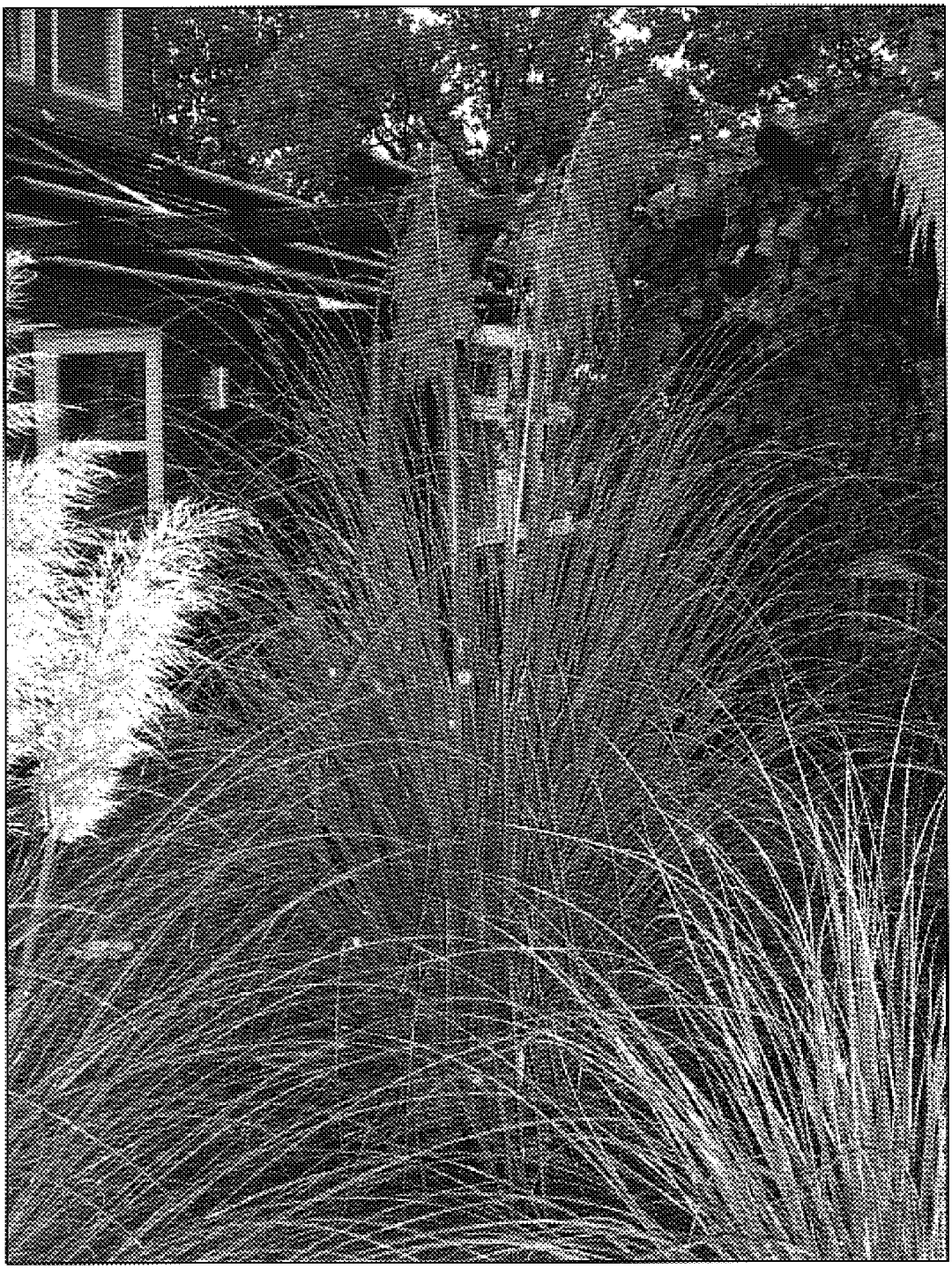

* * * * *